(12) United States Patent
Jensen (10) Patent No.: US 7,951,178 B2
(45) Date of Patent: May 31, 2011

(54) BONE PLATES WITH HYBRID APERTURES

(75) Inventor: David G. Jensen, Troutdale, OR (US)

(73) Assignee: Acumed LLC, Hillsboro, OR (US)

( * ) Notice: Subject to any disclaimer, the term of this patent is extended or adjusted under 35 U.S.C. 154(b) by 528 days.

(21) Appl. No.: 11/696,112

(22) Filed: Apr. 3, 2007

(65) Prior Publication Data

US 2008/0051786 A1 Feb. 28, 2008

Related U.S. Application Data

(60) Provisional application No. 60/789,111, filed on Apr. 3, 2006.

(51) Int. Cl.
*A61B 17/80* (2006.01)

(52) U.S. Cl. ...................................... 606/291

(58) Field of Classification Search ............... 606/69, 606/61, 73, 280–299
See application file for complete search history.

(56) References Cited

U.S. PATENT DOCUMENTS

| | | | |
|---|---|---|---|
| 4,408,601 A | 10/1983 | Wenk | |
| 5,041,113 A | 8/1991 | Biedermann et al. | |
| 5,085,660 A | 2/1992 | Lin | |
| 5,380,327 A | 1/1995 | Eggers et al. | |
| 5,534,027 A | 7/1996 | Hodorek | |
| 5,591,166 A | 1/1997 | Bernhardt et al. | |
| 5,601,553 A | 2/1997 | Trebing et al. | |
| 5,643,261 A | 7/1997 | Schafer et al. | |
| 5,643,265 A | 7/1997 | Errico et al. | |
| 5,709,686 A | 1/1998 | Talos et al. | |
| 5,735,853 A | 4/1998 | Olerud | |
| 5,807,396 A | 9/1998 | Raveh | |
| 5,810,823 A | 9/1998 | Klaue et al. | |
| 5,904,683 A | 5/1999 | Pohndorf et al. | |
| 5,954,722 A | 9/1999 | Bono | |
| 5,968,046 A | 10/1999 | Castleman | |
| 6,129,730 A | 10/2000 | Bono et al. | |
| 6,152,927 A | 11/2000 | Farris et al. | |
| 6,235,033 B1 | 5/2001 | Brace et al. | |
| 6,235,034 B1 | 5/2001 | Bray | |
| 6,261,291 B1 | 7/2001 | Talaber et al. | |
| 6,273,889 B1 | 8/2001 | Richelsoph | |
| 6,283,969 B1 | 9/2001 | Grusin et al. | |
| 6,290,703 B1 | 9/2001 | Ganem | |
| 6,315,779 B1 | 11/2001 | Morrison et al. | |
| 6,322,562 B1 | 11/2001 | Wolter | |
| 6,331,179 B1 | 12/2001 | Freid et al. | |
| 6,364,881 B1 | 4/2002 | Apgar et al. | |
| 6,379,354 B1 | 4/2002 | Rogozinski | |
| 6,402,756 B1 | 6/2002 | Ralph et al. | |
| 6,428,542 B1 | 8/2002 | Michelson | |
| 6,436,103 B1 | 8/2002 | Suddaby | |
| 6,440,135 B2 | 8/2002 | Orbay et al. | |
| 6,454,769 B2 | 9/2002 | Wagner et al. | |
| 6,454,770 B1 | 9/2002 | Klaue | |
| 6,458,133 B1 | 10/2002 | Lin | |

(Continued)

FOREIGN PATENT DOCUMENTS

WO 2005/082115 9/2005

*Primary Examiner* — Thomas C Barrett
*Assistant Examiner* — Michael J Araj
(74) *Attorney, Agent, or Firm* — Kolisch Hartwell, PC (57) ABSTRACT

Systems, including methods, apparatus, and kits, for fixing bones with bone plates having hybrid apertures.

18 Claims, 4 Drawing Sheets

U.S. PATENT DOCUMENTS

| | | |
|---|---|---|
| 6,623,486 B1 | 9/2003 | Weaver et al. |
| 6,669,701 B2 | 12/2003 | Steiner et al. |
| 6,730,091 B1 | 5/2004 | Pfefferle et al. |
| 6,821,278 B2 | 11/2004 | Frigg et al. |
| 7,776,076 B2 * | 8/2010 | Grady et al. .................. 606/291 |
| 2002/0004660 A1 | 1/2002 | Henniges et al. |
| 2002/0058940 A1 * | 5/2002 | Frigg et al. ...................... 606/69 |
| 2002/0128654 A1 | 9/2002 | Steger et al. |
| 2002/0183752 A1 | 12/2002 | Steiner et al. |
| 2002/0188296 A1 * | 12/2002 | Michelson ...................... 606/71 |
| 2004/0073218 A1 | 4/2004 | Dahners |
| 2005/0015089 A1 | 1/2005 | Young et al. |
| 2005/0070904 A1 * | 3/2005 | Gerlach et al. .................. 606/69 |
| 2005/0080421 A1 * | 4/2005 | Weaver et al. .................. 606/69 |
| 2005/0165400 A1 | 7/2005 | Fernandez |
| 2005/0192577 A1 * | 9/2005 | Mosca et al. .................... 606/69 |
| 2005/0192578 A1 | 9/2005 | Horst |
| 2005/0277937 A1 * | 12/2005 | Leung et al. .................... 606/69 |
| 2006/0122602 A1 * | 6/2006 | Konieczynski et al. ........ 606/69 |
| 2006/0129151 A1 * | 6/2006 | Allen et al. ..................... 606/69 |
| 2007/0239163 A1 * | 10/2007 | Strnad et al. .................... 606/72 |

* cited by examiner

BONE PLATES WITH HYBRID APERTURES

CROSS-REFERENCE TO PRIORITY APPLICATION

This application claims priority under 35 U.S.C. §119(e) to U.S. Provisional Patent Application Ser. No. 60/789,111, filed Apr. 3, 2006, which is incorporated herein by reference in its entirety for all purposes.

CROSS-REFERENCES TO RELATED MATERIALS

This application incorporates herein by reference the following U.S. Pat. No. 7,090,676, issued Aug. 15, 2006; U.S. Pat. No. 7,153,309, issued Dec. 26, 2006; and U.S. Pat. No. 7,189,237, issued Mar. 13, 2007.

This application incorporates herein by reference the following U.S. patent applications: Ser. No. 10/717,015, filed Nov. 19, 2003; Ser. No. 10/717,399, filed Nov. 19, 2003; Ser. No. 10/731,173, filed Dec. 8, 2003; Ser. No. 10/873,522, filed Jun. 21, 2004; Ser. No. 10/968,850, filed Oct. 18, 2004; Ser. No. 11/071,050, filed Feb. 28, 2005; Ser. No. 11/109,985, filed Apr. 19, 2005; Ser. No. 11/112,858, filed Apr. 22, 2005; and Ser. No. 11/330,802, filed Jan. 11, 2006.

BACKGROUND

The human skeleton is composed of 206 individual bones that perform a variety of important functions, including support, movement, protection, storage of minerals, and formation of blood cells. To ensure that the skeleton retains its ability to perform these functions, and to reduce pain and disfigurement, bones that become fractured should be repaired promptly and properly. Typically, a fractured bone is treated using a fixation device, which reinforces the fractured bone and keeps it aligned during healing. Fixation devices may take a variety of forms, including casts and fixators for external fixation, and bone plates and bone screws for internal fixation, among others.

Bone plates are implants that may be positioned under skin and other soft tissue for mounting on the bone adjacent the fracture. These plates may be manufactured and/or custom bent for mounting to particular regions of bone. To use a bone plate to repair a fractured bone, a surgeon (1) selects an appropriate plate, (2) reduces (sets) the fracture, and (3) fastens the plate to the bone on opposite sides of the fracture using suitable fasteners, such as bone screws, so that fragments of the bone are fixed in position.

Bone plates generally include a plurality of apertures sized and shaped to receive fasteners, such as bone screws. Each aperture of a bone plate may function as a nonlocking aperture or a locking aperture.

A nonlocking aperture generally receives a nonlocking fastener without threaded (or other locking) engagement between the bone plate and the fastener. For example, the nonlocking aperture may receive an undersized "toggle" fastener at a range of permitted angles or a close-fitting fastener at a predefined, fixed angle. In either case, the nonlocking fastener relies on bone to maintain engagement between the nonlocking fastener and the bone plate, for example, with the nonlocking fastener holding the bone plate in position against bone by engagement of the underside of a head of the nonlocking fastener with the bone plate.

A locking aperture may receive a locking fastener such that the locking fastener is disposed in a locked configuration. The locked configuration may be provided by a thread-engagement structure (such as an internal thread) of the locking aperture that is meshed with an external thread of the locking fastener. The locking fastener thus may be restrained from translational motion relative to the bone plate in both axial directions defined by the long axis of the locking fastener, to hold the bone plate in position and restrict plate motion both toward and away from bone.

Locked engagement and nonlocked engagement of fasteners with bone plates both have advantages for particular applications. However, each aperture of a bone plate generally is configured and/or optimized for use with either a nonlocking (e.g., toggle) fastener or a locking fastener, but not both.

SUMMARY

The present disclosure provides systems, including methods, apparatus, and kits, for fixing bones with bone plates having hybrid apertures.

DETAILED DESCRIPTION

The present disclosure provides systems, including methods, apparatus, and kits, for fixing bones with bone plates having hybrid apertures. Each bone plate may have at least one hybrid aperture for alternative use with a locking fastener and a nonlocking fastener (e.g., a toggle fastener). The hybrid aperture may have a locking portion, such as an internal thread, that engages an external thread of a locking fastener, to restrict both inward and outward translational motion of the locking fastener relative to the bone plate (and generally to fix the angle of the locking fastener). The hybrid aperture also may have a countersink portion disposed outward of the locking portion (i.e., disposed generally toward the outer face of the bone plate from the locking portion).

The countersink portion may have distinct recessed regions of different shape for respectively receiving at least a portion of the heads of locking and nonlocking fasteners. For example, the countersink portion may have a relatively more cylindrical recess (relatively steeper side walls and an end wall more approximately orthogonal to the side walls) for receiving at least a lower portion of a head of a locking fastener and a relatively more spherical recess (relative shallower side walls and substantially no end wall) for receiving at least a lower portion of a head of a nonlocking fastener. Alternatively, or in addition, the countersink portion may have a relatively more planar surface region for engagement with a relatively more planar bearing surface of a head of a locking fastener, and a relatively more concave surface region (such as a frustospherical region) for engagement with a relatively more convex bearing surface of a head of a nonlocking fastener. Accordingly, each type of fastener may be seated more effectively in the hybrid aperture using a distinct countersink surface region of the aperture that is configured to be more complementary to the shape of fastener head to be engaged. The system of the present disclosure thus may provide one or more advantages for bone fixation, such as greater flexibility in fastener selection, a more optimized fit for both locking and nonlocking fasteners in the same aperture, less protrusion of fastener heads above bone plates, and/or improved attachment of bone plates to bone, among others.

Figure 1:
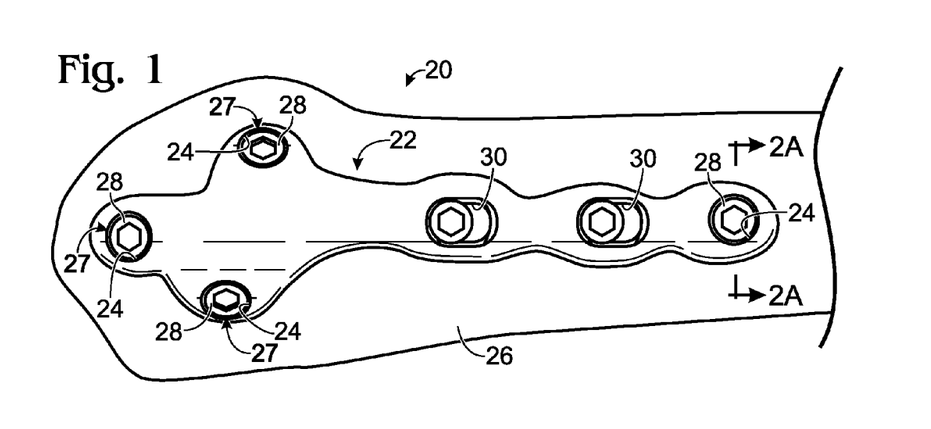
FIG. 1 is a plan view of an exemplary system for bone fixation including a bone plate with hybrid apertures that is secured to a bone at least in part via bone screws received in the hybrid apertures, in accordance with aspects of the present disclosure.

FIG. 1 shows an exemplary system 20 for bone fixation including a bone plate 22 with hybrid apertures 24. Bone plate 22 may be secured to a bone 26 such as a long bone at least in part via one or more fasteners 27, such as bone screws 28, received in the hybrid apertures. The bone plate also may have one or more other apertures that are not hybrid apertures, such as noncircular apertures (slots 30) and/or other circular apertures.

Figure 2A:
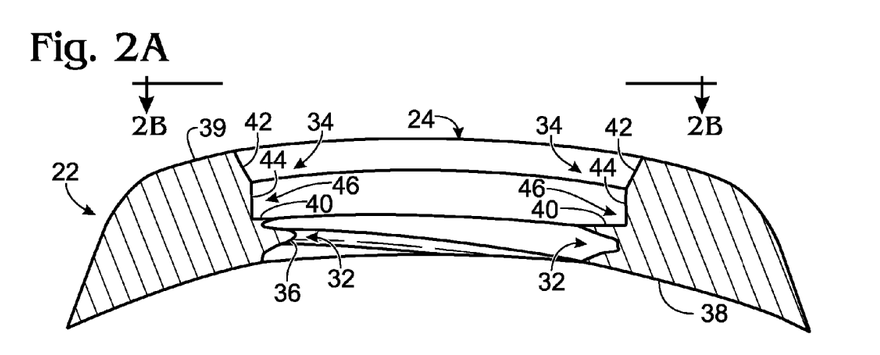
FIG. 2A is a sectional view of the bone plate of FIG. 1, taken generally along line 2A-2A of FIG. 1 through a hybrid aperture without its corresponding bone screw and in the absence of bone.
Figure 2B:
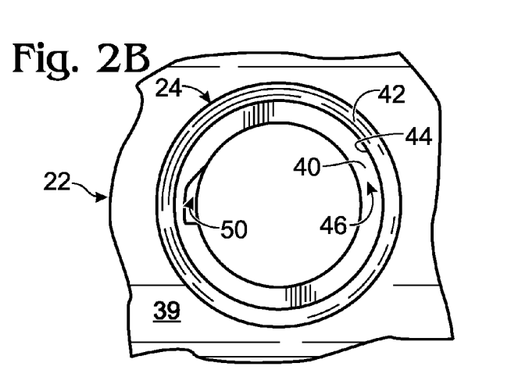
FIG. 2B is a plan view of the bone plate and hybrid aperture of FIG. 2A, taken generally along line 2B-2B of FIG. 2A.

FIGS. 2A and 2B show, respectively, a sectional view of a hybrid aperture of bone plate 22 and a view of the hybrid aperture from above the bone plate. The hybrid aperture may have a locking portion 32 and a countersink portion 34 disposed outward of the locking portion. The locking portion may include a thread-engagement structure, such as an internal thread 36, that engages a locking fastener such that the locking fastener is locked to the bone plate. The term "locked," as used herein, means that both inward and outward translational motion of the fastener is restricted by engagement with the bone plate. The terms "inward" and "outward," as used herein, are intended to denote the relative position of aperture structures. In particular, "inward" means toward or relatively closer to an inner surface or inner face 38 of the bone plate, and "outward" means toward or relatively closer to an outer surface or outer face 39 of the bone plate.

Countersink portion 34 may have a hybrid structure that accommodates distinct types of fasteners, particularly locking fasteners and nonlocking fasteners with heads having distinct shapes. For example, the countersink portion may include a relatively more planar surface region 40 and a relatively more concave surface region 42 (e.g., disposed at a relatively steeper angle to the inner and outer faces than the planar surface region).

Planar surface region 40 may have any suitable structure and disposition. For example, the planar surface region may abut a relatively cylindrical wall 44 (i.e., with a wall extending at a steeper angle (more orthogonally) than concave surface region 42) to create a cylindrical counterbore or cylindrical recess 46 of the countersink. In addition, the planar surface region may abut the locking portion of the aperture or may be spaced from the locking portion, for example, separated from the locking portion by at least a portion of the concave surface region. Furthermore, the planar surface region may be generally parallel to inner face 38 and/or opposing outer face 39 of the bone plate or may be oblique thereto, such as for seating an obliquely disposed locking fastener.

The concave surface region may have any suitable structure and disposition. For example, the concave surface region may be a flared wall that widens outwardly (toward the outer face of the bone plate). The concave surface region thus may have a relatively conical (e.g., frustoconical) and/or a relatively spherical (e.g., frustospherical) concave shape. The concave surface region may be disposed inward or outward of the planar surface region, or both inward and outward of the planar surface region.

The locking portion of the hybrid aperture may have any suitable relationship to the planar surface region. For example, the locking portion may intersect the planar surface region, indicated at 50 in FIG. 2B. Alternatively, or in addition, the locking portion may have a smaller inner diameter than the planar surface region, such that the locking portion projects radially inward from the planar surface region.

Figure 3:
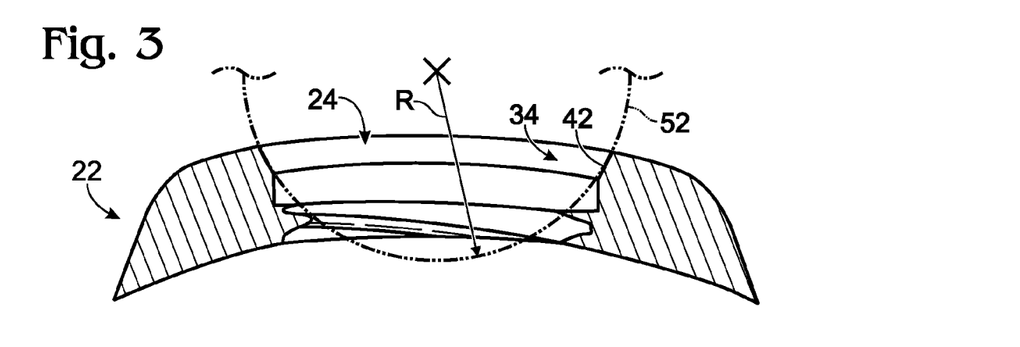
FIG. 3 is a sectional view of the bone plate of FIG. 1, taken as in FIG. 2A through the bone plate and hybrid aperture and with a frustospherical region of a countersink portion of the hybrid aperture abutted with a sphere (dashed).
Figure 4:
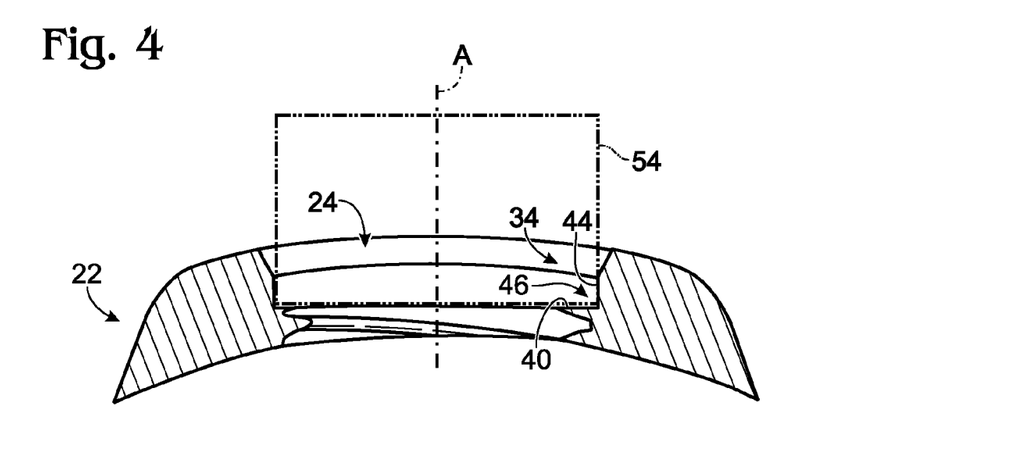
FIG. 4 is a sectional view of the bone plate of FIG. 1, taken as in FIG. 2A through the bone plate and hybrid aperture and with a cylindrical region of the countersink portion of the hybrid aperture abutted with a cylindrical disk (dashed).

FIGS. 3 and 4 show hybrid aperture 24 abutted with a pair of geometrical objects (dashed) to indicate the distinct surface and recessed regions of countersink portion 34. In FIG. 3, concave surface region 42 is abutted with a sphere 52 of radius "R" to show the frustospherical shape of the concave surface region. In FIG. 4, cylindrical recess 46 is abutted with a cylindrical disk 54 having a central axis "A" to show the planar shape of planar surface region 40 and the cylindrical shape of cylindrical wall 44.

Figure 5:
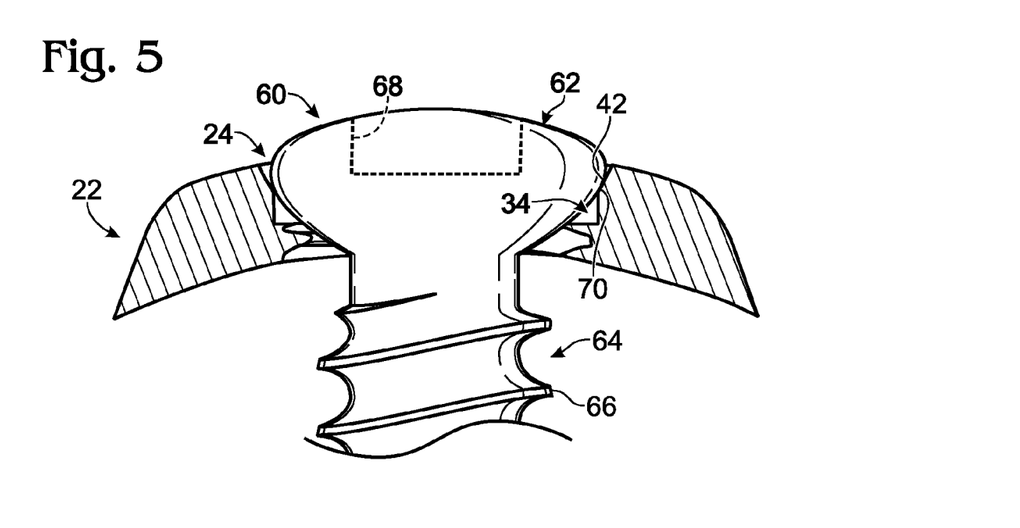
FIG. 5 is a sectional view of the bone plate of FIG. 1, taken as in FIG. 2A through the bone plate and hybrid aperture and with an exemplary toggle fastener seated in the hybrid aperture and presented in fragmentary view, in accordance with aspects of the present disclosure.

FIG. 5 shows hybrid aperture 24 engaged with an exemplary nonlocking (toggle) fastener 60. The term "toggle," as used herein for describing a fastener in conjunction with an aperture, means that the fastener can be seated in the aperture at a range of permitted angles. Toggle fastener 60 may be a bone screw include a head 62 connected to a shank 64 having an external thread 66. The head may define a driver-engagement structure, such as a socket 68, for receiving a driver that drives the toggle fastener into bone. Furthermore, the head may have a bearing surface 70 that engages concave surface region 42 of countersink portion 34 when the toggle fastener is advanced to its fully installed configuration in bone and against the bone plate. The bearing surface may correspond to an undersurface and/or a generally inward- or bone-facing surface of the head. The bearing surface may be and/or may be included in a convex surface of the head that is generally complementary to the concave surface region of the countersink portion. For example, the bearing surface of the head may be a convex frustospherical bearing surface for engagement with a concave frustospherical surface region of the countersink portion, generally with the frustospherical bearing surface and the frustospherical surface region corresponding to portions of respective spheres having about the same radius.

Figure 6:
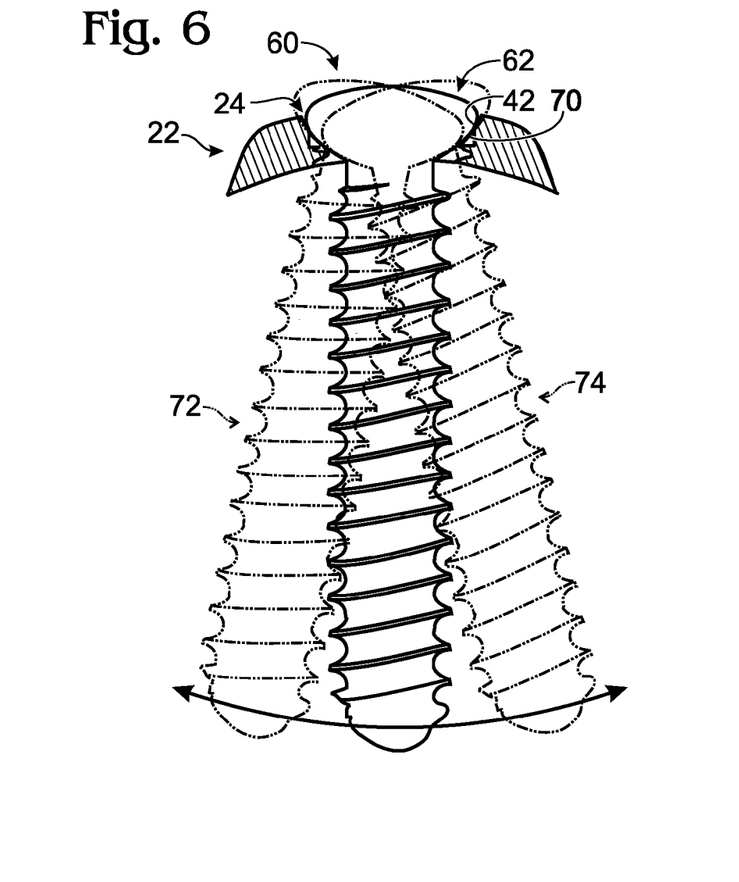
FIG. 6 is a sectional view of the bone plate, hybrid aperture, and toggle fastener of FIG. 5, with the toggle fastener disposed orthogonally to the bone plate, shown in solid lines, and at two other exemplary angular dispositions, shown in dashed outline, in accordance with aspects of the present disclosure.

FIG. 6 shows toggle fastener 60 disposed orthogonally to the bone plate and in a pair of exemplary oblique angular dispositions, indicated at 72 and 74, that are permitted by the hybrid aperture. In some embodiments, bearing surface 70 of head 62 may achieve substantial contact with the concave surface region 42 of the countersink portion over a range of angular dispositions because of the complementary spherical configurations of these surfaces.

Figure 7:
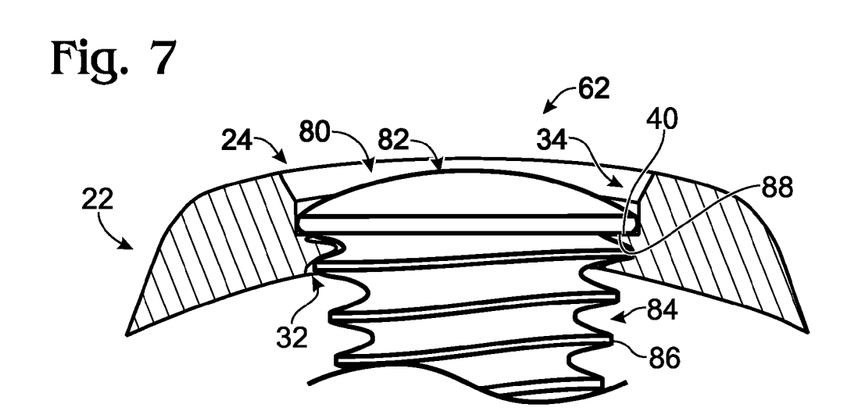
FIG. 7 is a sectional view of the bone plate of FIG. 1, taken as in FIG. 2A through the bone plate and hybrid aperture and with an exemplary locking fastener seated in the hybrid aperture and presented in fragmentary view, in accordance with aspects of the present disclosure.

FIG. 7 shows hybrid aperture 24 engaged with an exemplary locking fastener with 80. Locking fastener 80 may include a head 82 connected to a shank 84 having an external thread 86. The head may define a driver-engagement structure for receiving a driver that drives the locking fastener into bone. Furthermore, the head may have a bearing surface 88 that engages planar surface region 40 of aperture countersink 34 when the locking screw is advanced to its fully installed configuration in bone (and/or through the locking region of the aperture). The bearing surface may correspond to an undersurface and/or a generally inward- or bone-facing surface of the head. The bearing surface may be, may include, and/or may be included in a substantially (and/or relatively more) planar surface that engages the substantially (and/or relatively more) planar wall of the countersink portion. The external thread may threadably engage locking portion 32 of the hybrid aperture, to lock the locking fastener to the plate and, generally, to fix the angle of the locking fastener.

Locking fastener 80 may have any suitable structure. For example, shank 84 may flare as the shank extends toward the head of the locking fastener, such that the major diameter (and/or minor diameter) of external thread 86 increases towards the head. Accordingly, engagement of the external thread with the locking portion of the hybrid aperture may occur and/or may increase as the head of the locking fastener approaches engagement with the countersink portion of the hybrid aperture. Furthermore, the external thread may be a continuous thread that extends along at least a portion or all of the length of the shank. Alternatively, the locking fastener may have discrete threaded regions for engagement with bone and with the bone plate.

The following sections describe further aspects of the present disclosure, including, among others, (I) bone plates, (II) hybrid apertures, (III) fasteners for hybrid apertures, (IV) methods of fixing bones using bone plates with hybrid apertures, (V) kits for fixing bones using bone plates with hybrid apertures, and (VI) examples.

I. Bone Plates

Bone plates of the present disclosure generally comprise any plate-shaped fixation device configured for attachment to bone. The bone plates generally have a low enough profile on bone that they can be used for internal fixation, that is, with the bone plates disposed at least mostly or completely under the skin of plate recipients. The bone plates may be of a sturdy yet malleable construction. Generally, the bone plates should be stiffer and stronger than the section of bone spanned by each plate, yet flexible (e.g., springy) enough not to strain the bone significantly. The bone plates may be configured to reduce irritation to the bone and surrounding soft tissue. For example, the bone plates may have a low and/or feathered profile to reduce their protrusion into overlying soft tissue and rounded, burr-free surfaces to reduce the effects of such protrusion. The bone plates may have any suitable shape, structure, apertures, and composition, as described further below.

A. Bone Plate Shape and Structure

The bone plates of the present disclosure may have any shape suitable for use on their intended target bones. The bone plates may be shaped for use on any suitable bone or bones to be fixed, including a bone of the arms (such as a humerus, a radius, and/or an ulna), a bone of the legs (such as a femur, a tibia, and/or a fibula), a bone of the hands (such as a carpal, metacarpal, and/or phalange), a bone of the feet (such as a tarsal, metatarsal, and/or phalange), a clavicle, a rib, a scapula, a pelvic bone, a vertebra, and/or the like. The bone may have any suitable condition to be treated, including a fracture, a cut, a malunion, a nonunion, a structural weakness, an undesirable length and/or angulation, and/or the like. The condition may affect any suitable portion of the bone, such as a diaphyseal (shaft) and/or a metaphyseal (end) region of the bone.

Each bone plate may be configured for use on any suitable side or sides of the body. For example, the bone plate may be configured for use on both the left side and right side of the body/skeleton, such as when the bone plate has bi-lateral mirror symmetry. Alternatively, each bone plate may be configured for use on either the left side or right side of the body/skeleton, but not both.

Each bone plate may be shaped and sized for use on any position of a target bone. For example, the bone plate may be shaped for use near an end of a bone, with a stem or body portion of the bone plate disposed more centrally on a shaft of the bone, and a widened head portion of the bone plate disposed more towards a metaphyseal region (an end region) of the bone. Alternatively, the bone plate may lack a widened head portion, for example, if the bone plate is configured to be used more centrally on only a shaft of the bone.

Each bone plate may have any suitable contour. In some examples, the bone plate may be supplied in a pre-contoured configuration (e.g., by pre-operative bending, molding, and/or machining, among others) to include an inner surface that is complementary to a nonplanar surface region of a target bone. The bone plate thus may be pre-contoured according to an average or representative surface geometry of a target bone. Alternatively, or in addition, the bone plate may be contoured peri-operatively (e.g., by bending), to adjust its shape before and/or during its installation on bone, to improve, for example, the fit of the bone plate on a target bone for particular individuals and/or on distinct regions of the target bone.

The bone plate may have anchor portions (e.g., a head and a stem) connected to one another through a bridge or junction region. The junction region may be joined unitarily to each of the anchor portions, to provide a plate member of unitary construction, or may provide a site at which discrete plate components are connected to each other, to provide a plate member of non-unitary construction. The junction region may be configured to allow anchor portions of each plate to slide, bend, turn, and/or twist relative to one another. Alternatively, or in addition, the junction region may provide a site at which a guide device may be attached to the bone plate. Fasteners also or alternatively may be placed into bone through the junction region.

Each bone plate may be generally elongate (at least before bending), with a length L, a width W, and a thickness T. Here, length L>width W>thickness T. In use, the long axis of the bone plate may be aligned with the long axis of its target bone and/or may extend obliquely and/or transversely relative to the long axis. In some embodiments, the bone plate may have a length and a width that are about the same.

The thickness of the bone plate generally is defined by a distance between inner (bone-facing) and outer (bone-opposing) surfaces/faces of the plate. The thickness may be generally constant, at least locally within the bone plate, such that the inner and outer faces of the bone plate are generally complementary. Alternatively, the inner and outer faces may have distinct topographies, for example, an inner face that is concave and an outer face that is a combination of convex and planar. However, the thickness of the plate may vary according to the intended use, for example, to make the bone plate thinner as it extends over protrusions (such as processes, condyles, tuberosities, and/or the like), reducing its profile and/or rigidity, among others. The thickness of the bone plate also may be varied to facilitate use, for example, to make the plate thinner, to facilitate bending where it typically needs to be contoured peri-operatively. In this way, the plate may be thicker and thus stronger in regions where the plate typically does not need to be contoured, for example, regions of the plate that are placed along the shaft of the bone, among others. In some examples, the bridge region may be thinner than flanking anchor portions of the bone plate. A thinner bridge region may permit adjustment of the relative angular disposition of the anchor portions by bending and/or twisting the plate at the bridge region.

Each bone plate may be unitary or may include two or more discrete components. The two or more discrete components may be connected through a mechanical joint that enables translational and/or pivotal movement to adjust the shape and/or size of the bone plate. Further aspects of unitary and multi-component bone plates that are adjustable are described in the patents and patent applications listed above under Cross-References, which are incorporated herein by reference, particularly U.S. Pat. No. 7,090,676, issued Aug. 15, 2006; U.S. Pat. No. 7,189,237, issued Mar. 13, 2007; U.S. patent application Ser. No. 10/717,015, filed Nov. 19, 2003; and U.S. patent application Ser. No. 717,399, filed Nov. 19, 2003.

B. Bone Plate Apertures

The bone plates generally include a plurality of apertures (openings) configured to perform similar or different functions. The apertures may be adapted to receive fasteners for affixing the bone plates to bone. The apertures also or alternatively may function to alter the local rigidity of the bone plates and/or to facilitate blood flow to a fracture or surgical site to promote healing, among others. In some examples, one or more apertures of a bone plate may be configured for coupling a guide device and/or a compression-distraction device to the bone plate. Each aperture of a bone plate may have any suitable shape, including non-elongate (such as circular) or elongate (also termed oblong) (such as oval, elliptical, rectangular, etc.). Apertures may be created and/or tapped (threaded) pre-operatively, such as during the manufacture of the plates, and/or peri-operatively, such as with the plates disposed on bone. Further aspects of tapping apertures peri-operatively are described in U.S. patent application Ser. No. 10/873,522, filed Jun. 21, 2004, which is incorporated herein by reference.

A bone plate may have any suitable number and arrangement of hybrid apertures. The bone plate may have hybrid apertures only or may include one or more additional apertures that are not hybrid apertures. Further aspects of hybrid apertures are described elsewhere in the present disclosure, for example, in relation to the figures and in Section II.

Individual apertures may be locking or nonlocking. Exemplary locking apertures include a thread, ridge, groove, and/or flange for engaging relatively complementary thread structure on a fastener, to restrict translational movement of the fastener into and out of the aperture. The thread and/or a wall of the aperture also may be configured to stop over-advancement of a fastener. For example, the thread may terminate in a dead end adjacent the inner surface of the plate, and/or the thread or aperture wall may taper toward the inner face of the bone plate. Alternatively, or in addition, structure to stop over-advancement of the fastener may be included in the fastener, for example, on the head and/or a thread of the fastener. Other locking apertures are described in the patents and patent applications listed above under Cross-References, which are incorporated herein by reference, particularly U.S. patent application Ser. No. 11/071,050, filed Feb. 28, 2005.

The bone plates may have one or more openings configured as slots. A slot, also termed an oblong opening, is any opening having a length that is greater than its width. The slot may be linear, arcuate, or angled, among others. The slot (or any other type of bone plate aperture) may include a countersink structure to at least partially receive a head of a fastener. The countersink structure may be configured, as in a compression slot, to urge a fastener along the slot when the head of the fastener is advanced against the countersink structure. Slots may extend axially, that is, in general alignment with the long axis of the plate, obliquely, and/or generally crosswise to the long axis. Each bone plate may have one or more axial slots and one or more transverse slots. The slots may be used to adjust the translational and/or angular disposition of each bone plate on bone. Further aspects of slots that may be included in the bone plates of the present disclosure are described further in the patents and patent applications listed above under Cross-References, which are incorporated herein by reference, particularly, U.S. patent application Ser. No. 10/717,015, filed Nov. 19, 2003.

The bone plates may be configured to receive wires. Each bone plate thus may include one or more holes (generally of relatively smaller diameter) extending through the plate between inner and outer surfaces of the plate. Alternatively, or in addition, the bone plates may be configured to receive and retain wires that extend over (or under) the plates, rather than through the plates. Further aspects of bone plates configured to receive wires are described in the patents and patent applications listed above under References, which are incorporated herein by reference, particularly U.S. patent application Ser. No. 11/109,985, filed Apr. 19, 2005.

C. Plate Materials

A bone plate of the present disclosure may be substantially formed of any suitable biocompatible material(s) and/or bioresorbable (bioabsorbable) material(s). Exemplary biocompatible materials that may be suitable for the bone plate include (1) metals/metal alloys (for example, titanium or titanium alloys, cobalt-chrome alloys, stainless steel, etc.); (2) plastics (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) ceramics (for example, alumina, beryllia, calcium phosphate, and/or zirconia, among others); (4) composites (for example, carbon-fiber composites); (5) bioresorbable materials or polymers (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrimethylene carbonate, polyethylene oxide, poly-β-hydroxybutyrate, poly-β-hydroxypropionate, poly-δ-valerolactone, poly(hydroxyalkanoate)s of the PHB—PHV class, other bioresorbable polyesters, and/or natural polymers (such as collagen or other polypeptides, polysaccharides (e.g., starch, cellulose, and/or chitosan), any copolymers thereof, etc.); (6) bone material or bone-like material (e.g., bone chips, calcium phosphate crystals (e.g., hydroxyapatite, carbonated apatite, etc.); and/or the like. In some examples, one or more of these materials may form the body of a bone plate and/or a coating thereon.

Further aspects of bone plates that may be suitable for use in systems of the present disclosure are described in the patents and patent applications listed above under Cross-References, which are incorporated herein by reference, particularly U.S. Pat. No. 7,090,676, issued Aug. 15, 2006; U.S. Pat. No. 7,189,237, issued Mar. 13, 2007; U.S. patent application Ser. No. 10/717,015, filed Nov. 19, 2003; U.S. patent application Ser. No. 717,399, filed Nov. 19, 2003; U.S. patent application Ser. No. 10/731,173, filed Dec. 8, 2003; U.S. patent application Ser. No. 11/109,985, filed Apr. 19, 2005; U.S. patent application Ser. No. 11/112,858, filed Apr. 22, 2005; and U.S. patent application Ser. No. 11/330,802, filed Jan. 11, 2006.

II. Hybrid Apertures

The bone plates of the present disclosure may include one or more hybrid apertures. A hybrid aperture, as used herein, is any aperture having a locking portion and a countersink portion structured for engagement with fastener heads of different shape.

A hybrid aperture may have any suitable shape. The hybrid aperture may be circular when viewed in a direction normal to the outer face of the bone plate, or may be oblong, such as an oval-shaped hybrid aperture. Exemplary locking structure that may be suitable for oblong hybrid apertures is described in the following patent application, which is incorporated herein by reference: U.S. patent application Ser. No. 11/071,050, filed Feb. 28, 2005.

A hybrid aperture may include a countersink portion. The countersink portion may be configured to receive at least a portion, at least most, or all of a fastener head. Accordingly, the countersink portion may allow the head of the fastener to advance farther (relative to without the countersink portion), such that head does not protrude or protrudes less above the outer face of the bone plate. The countersink portion may include at least two distinct seating surfaces for engagement of fastener heads having different shapes. One of the seating surfaces may be relatively more planar than the other seating surface, which may be relatively more concave. In some examples, the planar seating surface may be formed by a relatively cylindrical counterbore. The counterbore may extend over any suitable fraction of the depth of the countersink, such as at least about one-tenth, one-fifth, or one-half, among others. The counterbore may be inward of, outward of, or within (i.e., interrupting or dividing) a flared region of the countersink portion.

A hybrid aperture may have any suitable locking portion. The locking portion may extend over any suitable portion of the depth of the aperture, such as at least about one-fifth or one-half, among others. In addition, the locking portion may have any suitable locking structure for engagement with a fastener thread. The locking structure may include, for example, an internal thread or thread-like structure (e.g., a linear or circular groove(s) or flange(s)). The thread or thread-like structure may extend around any suitable portion of the aperture or may extend completely around the hybrid aperture, one or more times.

A hybrid aperture may have any suitable disposition in a bone plate. For example, the hybrid aperture may be disposed in an anchor portion or a bridge region of the bone plate. In some embodiments, the bone plate may include at least one hybrid aperture in each anchor portion of the plate. In some embodiments, the bone plate may include one or more hybrid apertures in one anchor portion (e.g., a head portion of the bone plate) and may include no hybrid apertures in another anchor portion (e.g., a stem portion of the bone plate). Hybrid apertures may be more suitable for use near the end of the bone where there is more cancellous bone and/or where a head portion of the bone plate may be disposed.

III. Fasteners for Hybrid Apertures

Fasteners suitable for use with hybrid apertures generally comprise any mechanism for affixing a bone plate to a bone, including screws, pins, and/or wires, among others. Bone screws may include unicortical, bicortical, and/or cancellous bone screws. Unicortical and bicortical bone screws typically have relatively small threads for use in hard bone, such as is typically found in the shaft portion of a bone, whereas cancellous bone screws typically have relatively larger threads for use in soft bone, such as is typically found near the ends (metaphyseal regions) of a long bone. Unicortical bone screws penetrate the bone cortex once, adjacent the bone plate, whereas bicortical bone screws penetrate the bone cortex twice, once adjacent the bone plate and again opposite the bone plate. Generally, unicortical screws provide less support than bicortical screws, because they penetrate less cortex. The size and shape of the fasteners may be selected based on the size, shape, and/or locking portion of the hybrid apertures, or vice versa.

Each fastener placed into a hybrid aperture may have at least one an external thread. The external thread may be formed on a shank and/or a head of the fastener. The external thread may be one thread (single-threaded) or a plurality of threads (e.g., double-threaded, triple-threaded, etc.). The threads may be interspersed, so that the shank is multi-threaded with a plurality of thread leads, for example, to accommodate a greater pitch (a steeper thread angle). Alternatively, or in addition, the threads may be disposed on adjacent and/or nonoverlapping regions of the shank and/or head. The pitch of a thread may be constant along the shank/head, or may change either continuously or discontinuously according to position. For example, the pitch may decrease (or increase) toward a head of the fastener, to provide compression (or distraction) of the bone as the fastener is advanced into the bone. In some embodiments, the external thread may be two or more discrete threads with different pitches, such as a leading thread with a greater pitch, and a trailing thread with a lesser pitch, or vice versa.

In some embodiments, the thread of a locking fastener may have an at least substantially constant pitch along the shank of the locking fastener. In these embodiments, the rate of advancement of the threaded shank into bone may be at least substantially equal to the rate of advancement of the threaded shank through the hybrid aperture, to restrict compression of the bone plate against the bone and to preserve any desired spacing between the plate and the bone as the locking fastener is fully advanced into the aperture. The pitch of a thread on a threaded shank may be selected according to the locking portion of the hybrid aperture.

The fasteners may have any suitable linear density of thread revolutions (or linear densities, if multi-threaded). These densities may be measured using units, for example, such as number of thread revolutions per inch and/or meter, among others. For example, the fastener may have 16, 20, 24, 28, 32, 36, 40, and/or other numbers of thread revolutions per inch, among others; these linear densities correspond to thread-to-thread spacings (or pitches) of 0.0625 inches, 0.0500 inches, 0.0417 inches, 0.0357 inches, 0.03125 inches, 0.0278 inches, 0.0200 inches, and/or other fractions of an inch.

The threaded portions of fasteners may have any suitable diameters, including major (crest-to-crest) and minor (root-to-root) diameters. In some embodiments, the major diameters may be between about 1 to 10 mm. Exemplary major diameters include 1 mm, 1.5 mm, 2.0 mm, 2.7 mm, 3.5 mm, and 4.0 mm. In some embodiments, the difference between the major and minor diameters (generally, twice the thread height) may be in the range of about 0.1 mm to 5 mm, or in the range of about 0.2 mm to 2 mm. In some embodiments, the major diameter and minor diameter of the threaded portion may be generally constant along the fastener (e.g., along the length of the shank). In other embodiments, these diameters may be different in different portions of the fastener. For example, a proximal region of the shank (adjacent the head of the fastener) may have both a greater major and a greater minor diameter than a distal region of the shank, to permit selective coupling of the proximal region to a locking aperture.

Each fastener to be placed in a hybrid aperture may have a head. As head, as used herein, is a widened region of the fastener, generally disposed near the trailing end of the fastener. The head may include or lack an external thread. In addition, the head may have any suitable tool engagement structure, such as a polygonal recess, a polygonal projection, a single slot, a pair of slots in a cruciform arrangement, etc.

IV. Methods of Fixing Bones Using Bone Plates with Hybrid Apertures

The present disclosure provides methods of fixing bones by installing bone plates with hybrid apertures on the bones. The methods may include any suitable subset or combination of the following steps, performed in any suitable order, and any suitable number of times. The steps may include (1) selecting a bone for fixation, (2) selecting a bone plate with one or more hybrid apertures, (3) reducing a discontinuity in the bone, and (4) securing the bone plate to the bone, in part by installing a locking fastener and/or a nonlocking fastener (e.g., a toggle fastener) in the hybrid aperture(s). Securing the bone plate to bone may include (A) obtaining a locking fastener(s) and/or a toggle fastener(s) for use with the hybrid aperture(s), (B) selecting a locking fastener or a toggle fastener, and (C) installing the fastener selected.

A bone may be selected for fixation. The bone may have a discontinuity, such as a fracture or a cut, among others. The bone may be a long bone or another bone of the skeleton. In some embodiments, selecting a bone may include creating an incision through soft tissue on the anterior, posterior, lateral, and/or medial side of a limb, and in a proximal, distal, and/or central region of the limb, to access the bone. These and other suitable steps of the methods may be performed under sterile conditions and/or in a sterile field, for example, during surgery in an operating room.

A bone plate with one or more hybrid apertures may be selected for fixation of the selected bone. The bone plate may be selected according to the bone to be fixed and thus may have a size and shape corresponding to the bone. For example, the bone plate may be contoured (during manufacture and/or peri-operatively) so that its inner surface is nonplanar and is generally complementary to a nonplanar, exterior surface region of the bone. In some examples, the bone plate may be pre-contoured (e.g., by bending, machining, and/or casting, among others) according to an average or expected anatomy of a bone within a population. The bone plate may be configured for use on both sides of the skeleton, or may be configured for use on a right bone or a left bone, but not both. In some examples, the bone plate may include indicia (e.g., one or more alphanumeric characters, one or more words, a color, a bar code, etc.) to identify the bone plate, the bone for which the bone plate is configured, the size of the bone plate, the handedness of the bone plate, and/or the like.

The discontinuity in the bone may be reduced. Reduction may be performed before, during, and/or after the bone is exposed surgically.

The bone plate may be secured to the bone, before, during, and/or after reduction. (Bone plates secured before or during reduction typically would be secured only partially until the reduction is completed, unless the bone plate has an adjustable shape while secured to bone.) Securing the bone plate may be performed by placing one or more fasteners, such as screws, wires, pins, etc., through openings of the bone plate and into the bone. Generally, the bone plate may be secured to opposing sides of a discontinuity, such as a fracture, in the bone by placing fasteners through openings in a pair of anchor portions of the bone plate that generally flank the discontinuity.

Securing the bone plate to bone may include placing a threaded fastener, particularly a locking fastener and/or a toggle fastener, into one or more hybrid apertures of the bone plate. The threaded fastener may be advanced by turning the fastener, such that the fastener extends through the hybrid aperture and into bone. The threaded fastener may be advanced until a head of the threaded fastener engages a wall of the hybrid aperture. In some examples, either a locking fastener or a toggle fastener may be selected for installation into a hybrid aperture of the bone plate. Selection of the locking or toggle fastener may be based on any suitable criteria, such as type of bone, type of bone injury, aperture position, practitioner preference, extent of injury, position of bone fragment(s), etc. In some examples, selection and installation may be repeated for two or more hybrid apertures of the bone plate. In particular, the same type of fastener (e.g., locking or toggle) may be selected and installed in each hybrid aperture, or a locking fastener may be selected and installed in one hybrid aperture and a toggle fastener may be selected and installed in another hybrid aperture of the same bone plate.

The bone plate may be secured permanently or temporarily. In some examples, the bone plate may be left in place indefinitely. In some examples, the bone plate may be removed at a suitable time, such as after sufficient healing has occurred.

V. Kits for Fixing Bones Using Bone Plates with Hybrid Apertures

The systems of the present disclosure may provide kits for bone fixation. The kits may include one or more bone plates with a hybrid aperture(s) (as described elsewhere in the present disclosure), fasteners for a hybrid aperture (such as one or more locking fasteners and/or one or more toggle fasteners), additional fasteners (such as screws, wires, pins, clamps, etc.) for securing the bone plate(s) to bone via the hybrid apertures and/or non-the hybrid apertures apertures, a guide device(s), a drill(s), a saw or related cutting tool, one or more compression-distraction devices, instructions for use, and/or the like. Some or all of the components of each kit may be provided in a sterile condition, such as packaged in a sterile container.

VI. Examples

The following examples describe selected aspects and embodiments of the present disclosure, particularly an exemplary bone plate with a hybrid aperture, and a kit including a bone plate with a hybrid aperture. These examples and the various features and aspects thereof are included for illustration and are not intended to define or limit the entire scope of the present disclosure.

Example 1

Exemplary Bone Plate With Hybrid Apertures

Figure 8:
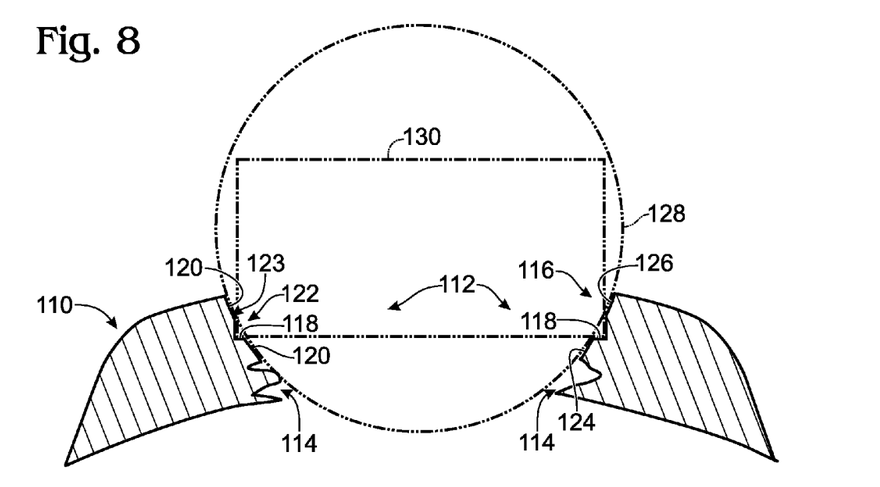
FIG. 8 is a sectional view of another exemplary bone plate, taken through a hybrid aperture of the bone plate, with the hybrid aperture including a nested pair of recessed regions for receiving fastener heads of different shape, as indicated by abutment of the recessed regions with a sphere and a cylindrical disk (each shown in phantom outline), in accordance with aspects of the present disclosure.

This example describes an exemplary bone plate 110 with a hybrid aperture 112; see FIG. 8. This sectional view presented here omits all portions of the aperture that are outside of (both in front of and behind) the sectional plane, to simplify the presentation.

Hybrid aperture 112 may include a locking portion 114 disposed inward of a countersink portion 116. The locking portion may engage a threaded region of a locking fastener to lock the fastener to the bone plate. The countersink portion may include a relatively more planar surface region 118 disposed within relatively more concave surface region 120. In particular, planar surface region 118 may be formed by a counterbore or relatively cylindrical recess 122 that is nested in and interrupts/divides a relatively spherical recess 123. In particular, concave surface region 120 is divided by cylindrical recess 122 into an inner concave region 124 disposed inward of cylindrical recess 122 and planar surface region 118 and an outer concave region 126 disposed outward of the cylindrical recess 122 and planar surface region 118. For illustrative purposes, a sphere 128 is abutted against concave surface region 120, and a cylindrical disk 130 is abutted against the cylindrical recess, to indicate the ability of the countersink portion to receive at least a portion of fastener heads having different shapes.

Example 2

Exemplary Kit for Bone Fixation

Figure 9:
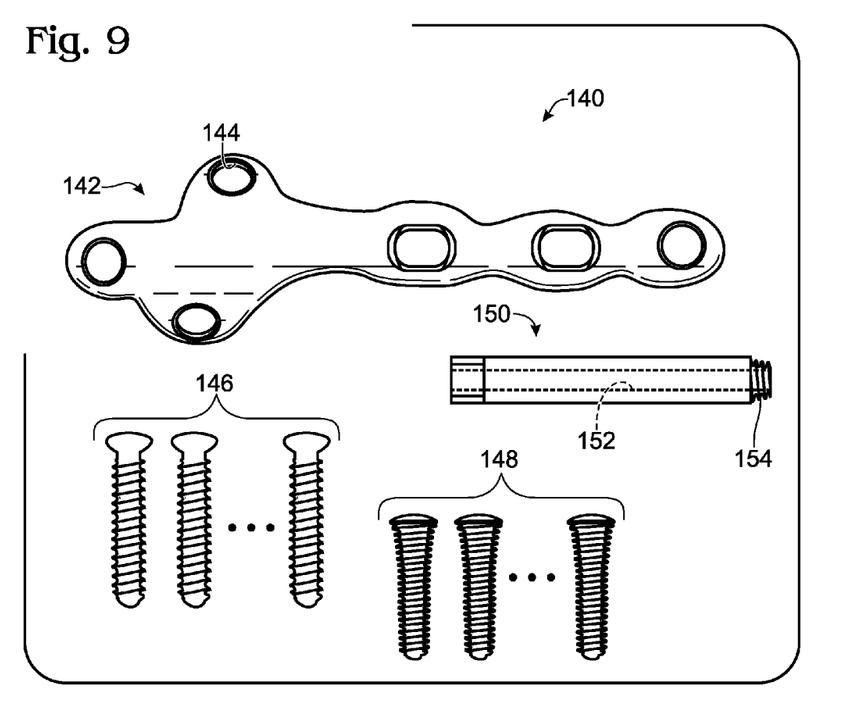
FIG. 9 is a view of an exemplary kit for bone fixation and including a bone plate with a plurality of hybrid apertures, locking and nonlocking fasteners for alternative placement into each hybrid aperture, and a drill guide, in accordance with aspects of the present disclosure.

This example describes an exemplary kit 140 for fixing bones using a bone plate 142 with one or more hybrid apertures 144; see FIG. 9.

The kit may include any other suitable components. For example, the kit may include one or more toggle bone screws 146, one or more locking bone screws 148, and a guide 150. The guide may be used to guide a wire, drill, screw, and/or driver in relation to a hybrid aperture. Accordingly, the guide may include a cannulation 152 and may have a threaded region 154 that engages a locking portion of a hybrid aperture, to position the guide and lock the guide to the bone plate.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A system for bone fixation, comprising:
a bone plate including opposing inner and outer faces and defining a plurality of apertures adapted to receive fasteners that secure the bone plate to bone, at least one of the plurality of apertures being a hybrid aperture including a locking portion for thread engagement and a countersink portion disposed toward the outer face from the locking portion, the countersink portion including a generally cylindrical recess and a relatively more spherical recess,
wherein the spherical recess is divided into an upper area and a lower area that are separated from one another by the generally cylindrical recess.

2. The system of claim 1, wherein the hybrid aperture is circular.

3. The system of claim 1, wherein the countersink portion includes a generally frustospherical wall that creates the relatively more spherical recess.

4. The system of claim 1, wherein the inner face of the bone plate is contoured during its manufacture to be complementary to a predetermined surface region of bone.

5. The system of claim 1, wherein the locking portion includes an internal thread.

6. The system of claim 1, wherein two or more of the plurality of apertures are hybrid apertures.

7. The system of claim 1, further comprising a locking fastener and a toggle fastener configured to be received alternatively in the hybrid aperture, wherein the locking fastener includes an external thread for threaded engagement with the locking portion of the bone plate and also includes a head configured to engage an end wall of the generally cylindrical recess if the locking fastener is seated in the hybrid aperture, and wherein the toggle fastener includes a head configured to engage a wall region of the relatively more spherical recess if the toggle fastener is seated in the hybrid aperture.

8. The system of claim 1, wherein the hybrid aperture defines a central axis that extends through the hybrid aperture, and wherein each of the recesses extends at least substantially completely around the central axis.

9. A system for bone fixation, comprising:
a toggle fastener having a head with a relatively more convex surface region;
a locking fastener having an external thread and also having a head with a relatively more planar surface region; and
a bone plate defining a plurality of apertures adapted to receive fasteners that secure the bone plate to bone, at least one of the plurality of apertures being a hybrid aperture for alternatively receiving the toggle fastener at a ranges of angles and the locking fastener at a fixed angle, the hybrid aperture having a locking portion for engagement with the external thread of the locking fastener and a countersink portion disposed above the locking portion, the countersink portion including a relatively more planar surface region for engagement of the relatively more planar surface region of the locking fastener, if the locking fastener is seated in the hybrid aperture, and a relatively more concave surface region for engagement with the relatively more convex surface region of the toggle fastener, if the toggle fastener is seated in the hybrid aperture, wherein the hybrid aperture defines a central axis that extends through the hybrid aperture, wherein each of the surface regions of the countersink portion extends at least substantially completely around the central axis, and wherein the concave surface region of the countersink portion is divided into an upper area and a lower area that are separated from one another by a counterbore that includes the planar surface region of the countersink portion.

10. The system of claim 9, wherein the locking fastener has a shank connected to the head of the locking fastener, wherein the shank has a length, and wherein the external thread extends along a majority of the length of the shank.

11. The system of claim 9, wherein the locking fastener includes an external thread, and wherein the external thread has a major diameter that increases toward the head of the locking fastener.

12. The system of claim 9, wherein the relatively more convex surface region of the toggle fastener is generally frustospherical.

13. The system of claim 9, wherein the relatively more convex surface region of the toggle fastener and the relatively more concave surface region of the countersink portion are complementary to one another.

14. The system of claim 9, wherein the relatively more planar surface region of the countersink portion is circumscribed by a substantially cylindrical wall such that the relatively more planar surface region of the countersink portion forms an end of the counterbore a cylindrical bore.

15. A method of bone fixation, comprising:

selecting a bone plate including a hybrid aperture having a locking portion for thread engagement and a countersink portion disposed above the locking portion, the countersink portion including a relatively more planar surface region and a relatively more concave surface region, wherein the concave surface region is divided into an upper area and a lower area that are separated from one another by a counterbore that includes the planar surface region, wherein the hybrid aperture defines a central axis that extends through the hybrid aperture, and wherein each of the surface regions extends at least substantially completely around the central axis; and placing (a) a locking fastener into the hybrid aperture of the bone plate and into bone such that the locking fastener is locked to the bone plate via the locking portion and such that a head of the locking fastener is engaged with the relatively more planar surface region of the countersink portion, or (b) a toggle fastener into the hybrid aperture of the bone plate and into bone such that a head of the toggle fastener is engaged with the relatively more concave surface region of the countersink portion.

16. The method of claim 15, wherein the step of placing includes a step of selectively engaging the head of the locking fastener with the relatively more planar surface region to the substantial exclusion of engagement with the relatively more concave surface region of the countersink portion.

17. The method of claim 15, wherein the step of placing includes a step of engaging the head of the toggle fastener with the relatively more concave surface region of the countersink portion.

18. The method of claim 17, wherein the step of placing includes a step of selecting an angle for toggle fastener placement from a range of permitted angles.

* * * * *